United States Patent
Bellettini et al.

(10) Patent No.: US 6,210,653 B1
(45) Date of Patent: Apr. 3, 2001

(54) METHOD FOR THE TREATMENT OF HIV INFECTED CELLS

(76) Inventors: Arturo G. Bellettini, 15 Cuervo Dr., Aliso Viejo, CA (US) 92656; Richard J. Bellettini, 330 N. Cordova St., Burbank, CA (US) 91505

(*) Notice: Subject to any disclaimer, the term of this patent is extended or adjusted under 35 U.S.C. 154(b) by 0 days.

(21) Appl. No.: 09/437,068

(22) Filed: Nov. 9, 1999

Related U.S. Application Data

(63) Continuation-in-part of application No. 08/954,154, filed on Oct. 20, 1997, now abandoned, and a continuation-in-part of application No. 08/413,221, filed on Mar. 30, 1995, now abandoned.

(51) Int. Cl.[7] ............................ A61K 51/00; A61M 36/14
(52) U.S. Cl. ...................... 424/1.73; 424/1.11; 424/1.65
(58) Field of Search .................................. 424/1.11, 1.37, 424/1.65, 9.1, 9.2, 1.73

(56) References Cited

U.S. PATENT DOCUMENTS

| | | |
|---|---|---|
| 2,835,655 | 5/1958 | Bauman . |
| 3,952,805 | 4/1976 | Persinski . |
| 5,026,490 | 6/1991 | Peiffer . |
| 5,342,646 * | 8/1994 | Kleese et al. ............................ 427/2.1 |

OTHER PUBLICATIONS

Baba et al, Antimicrobial Agents and Chemotherapy, vol. 32, No. 11, pp. 1742–1745, 'Sulfated Polysaccharide Are Potent and Selective Inhibitors of Various Enveloped Viruses, Including Herpes Simplex Virus, Cytomegalovirus, Vesicular Stomatitis Virus, and Human Immunodeficiency Virus', Nov. 1988.*

Mitsuya et al, Science, vol. 240, pp. 646–649, Dextran Sulfate Suppression of Viruses in the HIV Family: Inhibition of Virion Binding to CD4[+] Cells, Apr. 1988.*

Helenius et al, Biochimica et al Biophysica Acta, vol. 415, pp. 29–79, 'Solubilization of Membranes by Detergents', 1975.*

* cited by examiner

*Primary Examiner*—Dameron Jones

(57) ABSTRACT

Low molecular weight polystyrenes containing sulfonic acids and their salts or low molecular weight sulfonated polystyrene copolymers used as anti-viral agents against enveloped viruses such as HIV. These compounds have been shown to be effective in in vitro testing against HIV at subtoxic concentrations.

2 Claims, 1 Drawing Sheet

POLYSTYRENE SODIUM SULFONATE ANTIVIRAL ACTIVITY

POLYSTYRENE SODIUM SULFONATE ANTIVIRAL ACTIVITY

METHOD FOR THE TREATMENT OF HIV INFECTED CELLS

CROSS-REFERENCE TO RELATED APPLICATIONS

This application is a continuation in part of earlier application Ser. No. 08/413,221 filed Mar 30, 1995 abandoned and Ser. No. 08/954,154 filed Oct. 20, 1998 abandoned.

BACKGROUND OF THE INVENTION

1. Field of the Invention

This invention relates to the use of low molecular weight sulfonated polystyrenes or copolymers of these compounds with carboxylic containing monomers as selective anti-viral agents against HIV and other enveloped viruses.

2. Prior Art

Bauman et al U.S. Pat. No. 2,835,655 May 1958

Persinski et al U.S. Pat. No. 3,952,805 August 1976

Peiffer et al U.S. Pat. No. 5,026,490 June 1991

OTHER PUBLICATIONS

Babe M. et al. Antimicrobial agents-Chemother 1988; 32: 1742–5. Sulfated polysaccharides are potent selective inhibitors of various enveloped viruses.

Mitsuya H. Looney, D. J. Kunos et al. Science 1988; 240: 646–9. Dextran sulfated suppressive of viruses in the HIV family. A. Helenius and K Simos. Biochimica et Biophysica Acta, 415(1975) 29–79.

SUMMARY OF THE INVENTION

Sulfated and sulfonated compounds containing hydrophobic backbones are well known to solubilize viral and bacterial membranes. Compounds such as fatty sulfated alcohols have powerful solubilizing properties which are used to dissolve viral membranes, but these materials had no cell protection from HIV induced death and the dextran sulfates had comperatively low activity. However, the model polystyrene sodium solfonates had high activity and the activity was highest at 4600 molecular weight see Table 1 and FIG. 1.

We also tested sulfonated styrene maleic anhydride copolymers of very low molecular weight and these materials had also very high activity as they approached the 4600 molecular weight. It should be pointed out that the patent references of Bauman (column 3, lines 26–29), Persinski (column 4, lines 60–65), Peiffer (column 5, lines 32–35, 53–55), although disclosing a sulfonated styrene-maleic anhydride copolymer, failed to disclose their high anti-viral activity against the HIV virus at the low molecular weight range indicated above. These patents deal mainly with the synthesis of these compounds, Bauman U.S. Pat. No. 2,835,655 or their use in other applications Persinski U.S. Pat. No. 3,952,805 (Well cementing Method) and Peiffer U.S. Pat. No. 5,026,490 (Deflocculants in water based drilling fluids). We also studied the effect of polystyrene-maleic anhydride copolymers with molecular weight less than 10,000 and these materials not only had cell protection against HIV as indicated above, but they also had anti-viral activity against HIV-1 strain at subtoxic concentrations in plaque reduction assays with IC95's around 10 ug/ml. So these polymers not only protected the cells against HIV infection, but also attacked the virus itself.

The sulfonated polymers studied were made by well known methods involving sulfonation of polystyrene and polystyrene copolymers with sulfur trioxide in an appropiate solvent. The more active lower molecular weight fractions were obtained by separation using gel permeation techniques or were made directly from low molecular weight unsulfonated polymers.

We believe the anti-viral activity of these polymers is either due to the ability of these compounds to prevent attachment to the T cells and/or it is due to the ability of these polymers to complex with the virus and dissolve away the viral membrane exposing the harmless nuclocapsid. It should be mentioned that mamalian cells are not as susceptible to this type of disruption as are the viral and bacterial cells, and failure of the dextran sulfates and the sulfated fatty alcohols are due to the fact that the former does not have very hydrophobic backbones and the lattter have too low a molecular weight to be effective. In addition these styrene based polymers have very low toxicity to T-cells which makes them even more valuable as anti-viral agents. Table 1 shows that sulfonated polystyrene homopolymers have anti-viral activity against HIV although not as high as those of the sulfonated styrene maleic anhydride copolymers, similarly homopolymers of pure maleic anhydride have lower activity than the sulfonated styrene maleic anhydride copolymers with IC90 of 3.0.

BRIEF DESCRIPTION OF THE DRAWINGS

Table 1 shows anti-viral activity and cell toxicity data of selected compounds

DESCRIPTION OF THE PREFERRED EMBODIMENT

Figure 1:
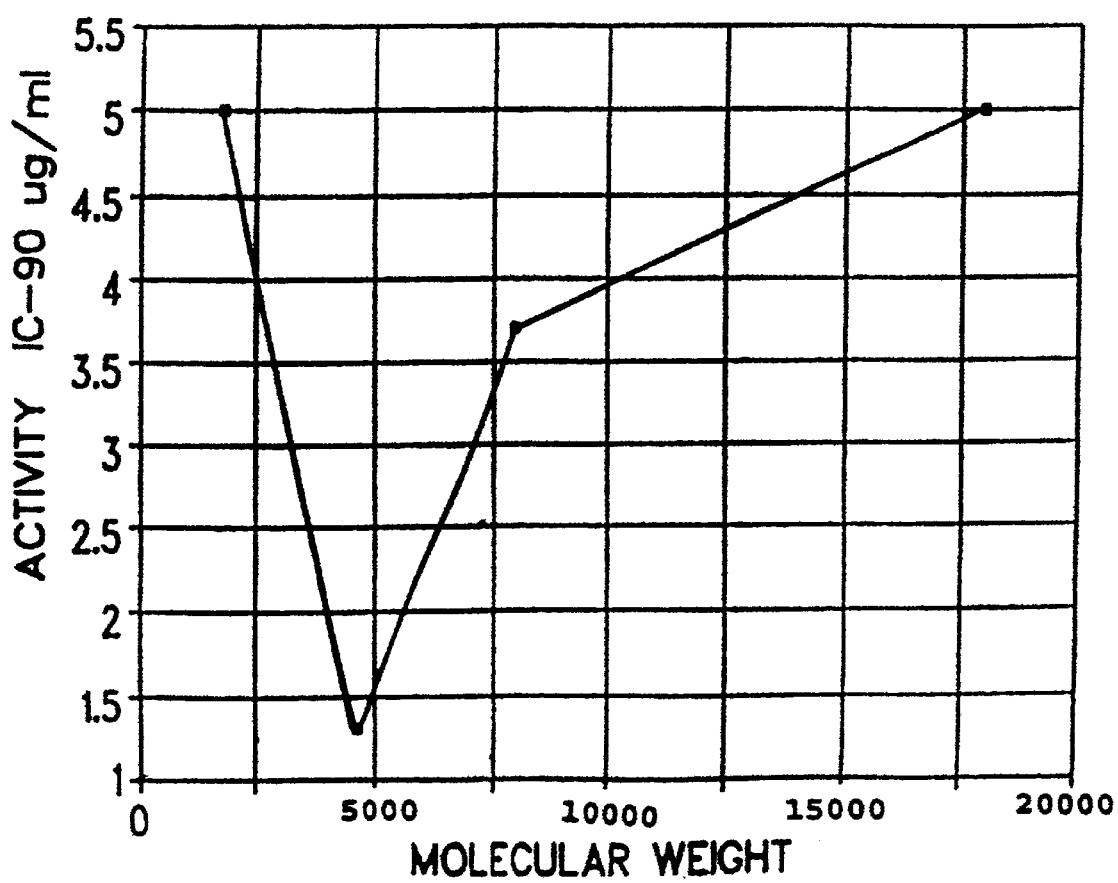
FIG. 1 is a graph showing anti-viral activity vs. molecular weight for polystyrene sodium sulfonate.

FIG. 1 shows an optimal anti-viral activity at 4600 molecular weight. This molecular weight to be employed in a copolymer of maleic anhydride and styrene containing a sulfonic acid group or its salts.

Many other variations are possible, for example one could add peptides, radioactive metal ions, or bile acids esters which by themselves also have powerful membrane disrupting activities. The addition of peptides would increase the polymers specificity towards the virus and the excellent chellating properties of these polymers would prevent the the radioactive salts from damaging non-target cells. The use of radionuclides of commercially available Cr-51, Cobalt-55 and Copper-67 will increase the anti-viral activity of the copolymers by acting by a different mechanism (gamma radiation) against virons such as HIV. In addition, the combination of any of these agents with the anti-viral polymer with an optimal molecular weight of 4600 would increase the activity of the polymers.

Accordingly, the scope of the invention should be determined not by the embodiment illustrated, but by the claims and their legal equivalents.

What is claimed is:

1. A method for treating HIV infected cells comprising administering a sulfonated styrene-maleic anhydride copolymer or a salt thereof with maleic anhydride content 0–95%.

2. A method for treating HIV infected cells using copolymers in claim 1 which contain radionuclides salts of Chromium-51, Cobalt-55 and Copper-67.

TABLE 1

Anti-viral Activity of Selected Compounds

| Compound | M. Wt. | μg/ml IC90 | TC50 |
|---|---|---|---|
| Polystyrene sodium sulfonate | 1800 | 5.0 | >50 |
| Polystyrene sodium sulfonate | 4600 | 1.3 | >50 |
| Polystyrene sodium sulfonate | 8000 | 3.7 | >50 |
| Polystyrene sodium sulfonate | 18000 | 5.0 | >50 |
| Polystyrene sodium sulfonate | 200000 | 23.1 | >50 |
| Sodium polystyrene maleic acid sulfonate (2/1) | 11000 | 0.14 | >50 |
| Sodium polystyrene maleic acid sulfonate (3/1) | 6100 | 0.07 | >50 |
| Sodium polystyrene maleic acid sulfonate (5.7/1) | 5800 | 0.12 | >50 |
| Dextran sulfate | 5000 | 3.0 | — |
| ddc~AZT | — | 0.3–0.6 | — |
| Fatty alcohol Sodium sulfate | 422 | NA | >50 |

IC90 = Concentration required to protect 90% of MT-2 cells from HIV induced death.
TC50 = Concentration required to reduce uninfected cell number by 50%
NA = Not Active

* * * * *